United States Patent
Mehta et al.

(10) Patent No.: US 12,064,765 B2
(45) Date of Patent: Aug. 20, 2024

(54) METHOD AND DEVICE FOR DETERMINING THE CONCENTRATION OF ANALYTES IN WHOLE BLOOD

(71) Applicant: Siemens Healthcare Diagnostics Inc., Tarrytown, NY (US)

(72) Inventors: Kalpesh Mehta, Singapore (SG); Mohiudeen Azhar, Bangalore (IN)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 752 days.

(21) Appl. No.: 17/264,487

(22) PCT Filed: Jul. 31, 2019

(86) PCT No.: PCT/US2019/044294
§ 371 (c)(1),
(2) Date: Jan. 29, 2021

(87) PCT Pub. No.: WO2020/033192
PCT Pub. Date: Feb. 13, 2020

(65) Prior Publication Data
US 2021/0291183 A1   Sep. 23, 2021

Related U.S. Application Data

(60) Provisional application No. 62/715,019, filed on Aug. 6, 2018.

(51) Int. Cl.
*B01L 3/00* (2006.01)
*B03C 5/00* (2006.01)
(Continued)

(52) U.S. Cl.
CPC ... *B01L 3/502753* (2013.01); *B01L 3/502761* (2013.01); *B03C 5/005* (2013.01);
(Continued)

(58) Field of Classification Search
None
See application file for complete search history.

(56) References Cited

U.S. PATENT DOCUMENTS 3,296,922 A   1/1967   Goldberg
5,478,479 A   12/1995   Herrig
(Continued)

FOREIGN PATENT DOCUMENTS

| JP | 2013022021 A | 2/2013 |
| WO | 2008124064 A1 | 10/2008 |
| WO | 2018065626 A1 | 4/2018 |

OTHER PUBLICATIONS

International Search Report and Written Opinion of International Application No. PCT/US2019/044294 dated Dec. 11, 2019.
(Continued)

*Primary Examiner* — J. Christopher Ball (57) ABSTRACT

A method and system for determining a concentration of one or more analytes in whole blood is provided. In one aspect of the invention, the system includes a channel configured to carry whole blood. The system further includes a light source configured to emit light on the channel. Additionally, the system includes an actuation module associable with the channel, wherein the actuation module is configured to generate a cell-free plasma layer in the channel. Furthermore, the system includes an optical module associable with the channel.

7 Claims, 5 Drawing Sheets

(51) Int. Cl.
    *B03C 5/02*         (2006.01)
    *G01N 21/17*      (2006.01)
    *G01N 21/31*      (2006.01)
    *G01N 27/447*     (2006.01)
    *G01N 33/49*      (2006.01)

(52) U.S. Cl.
    CPC ......... *B03C 5/024* (2013.01); *G01N 21/1717* (2013.01); *G01N 21/31* (2013.01); *G01N 27/44721* (2013.01); *G01N 27/44791* (2013.01); *G01N 33/4925* (2013.01); *B01L 2300/0645* (2013.01); *B01L 2300/0822* (2013.01); *B01L 2400/0424* (2013.01); *G01N 2021/1721* (2013.01)

(56) References Cited

U.S. PATENT DOCUMENTS

| | | |
|---|---|---|
| 8,883,513 B2 | 11/2014 | Pollack et al. |
| 9,535,053 B1 | 1/2017 | Cafferty et al. |
| 2016/0202237 A1 | 7/2016 | Zeng et al. |
| 2017/0248618 A1 | 8/2017 | Baxter et al. |
| 2019/0054465 A1 | 2/2019 | Hong et al. |

OTHER PUBLICATIONS

European Search Report and Written Opinion of European Application No. 19848214.3 dated Jul. 16, 2021.
Chen et al., "Microfluidic chip for plasma separation from undiluted human whole blood samples using low voltage contactless dielectrophoresis and capillary force", Mar. 8, 2014 (Mar. 18, 2014), Lab on a Chip, vol. 14; No. 12; 1, pp. 1996-2001.

METHOD AND DEVICE FOR DETERMINING THE CONCENTRATION OF ANALYTES IN WHOLE BLOOD

The subject application claims benefit under 35 USC § 119(e) of U.S. provisional Application No. 62/715,019, filed Aug. 6, 2018. The entire contents of the above-referenced patent application are hereby expressly incorporated herein by reference.

FIELD OF TECHNOLOGY

The present disclosure relates to the field of analysis of whole blood and more particularly to the field of determining the concentration of analytes in whole blood.

BACKGROUND

Hemolysis is a phenomenon wherein the blood cells rupture in whole blood, releasing their content into the blood plasma. This condition may occur due to various reasons such as immune reactions, infections, and medications. Hemolysis may occur within the body of an individual or after the blood has been extracted out of the body. A major cause of hemolysis is the pre-analytical steps of blood sample handling, including collection of the blood sample from the body of an individual. During hemolysis, the composition of the blood plasma is altered because of the contents of the blood cells spilling into the blood plasma. If the composition of the blood plasma is altered beyond a certain threshold, the blood sample is flagged for hemolysis. If the composition of the blood plasma is altered beyond a higher threshold, the blood sample may become incapable of further use and therefore has to be rejected.

Blood gas analysis, particularly co-oximetry is a method of measuring the oxygen carrying state of hemoglobin in whole blood. Co-oximetry includes analysis of oxygen carrying hemoglobin (O2Hb), non-oxygen carrying but normal hemoglobin (HHb), carboxyhemoglobin (COHb) and methemoglobin (MetHb). Co-oximetry is an essential method of identifying the causes of oxygen deficiency in blood.

The object of the invention is achieved by a method and a device for determining the concentration of analytes in whole blood.

SUMMARY

A device for determining a concentration of one or more analytes in whole blood is disclosed. In one aspect of the invention, the device includes a channel configured to carry the whole blood. The device further includes an actuation module associable with the channel. Additionally, the device includes a blood gas analysis module associable with the channel. Furthermore, the device includes a hemolysis detection module associable with the channel.

In another aspect, a method for determining the concentration of one or more analytes in whole blood includes flowing the whole blood through a channel. The method further includes measuring blood gas in the unseparated whole blood. Additionally, the method includes generating a plasma layer in the whole blood, the plasma layer being devoid of blood cells. Furthermore, the method includes detecting hemolysis in the generated plasma layer.

This summary is provided to introduce a selection of concepts in a simplified form that are further described below in the following description. It is not intended to identify features or essential features of the claimed subject matter. Furthermore, the claimed subject matter is not limited to implementations that solve any or all disadvantages noted in any part of this disclosure.

BRIEF DESCRIPTION OF THE DRAWINGS

The present invention is further described hereinafter with reference to illustrated embodiments shown in the accompanying drawings, in which.

DETAILED DESCRIPTION

Hereinafter, embodiments for carrying out the present invention are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details. In other instances, well known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the present disclosure.

Conventionally, co-oximetry and hemolysis measurements are performed separately as co-oximetry is performed on a whole blood sample, whereas hemolysis detection is performed on cell-free plasma. Therefore, the object of the invention is to provide a method and a system that is capable of performing blood gas analysis as well as hemolysis detection in a single device.

Figure 1:
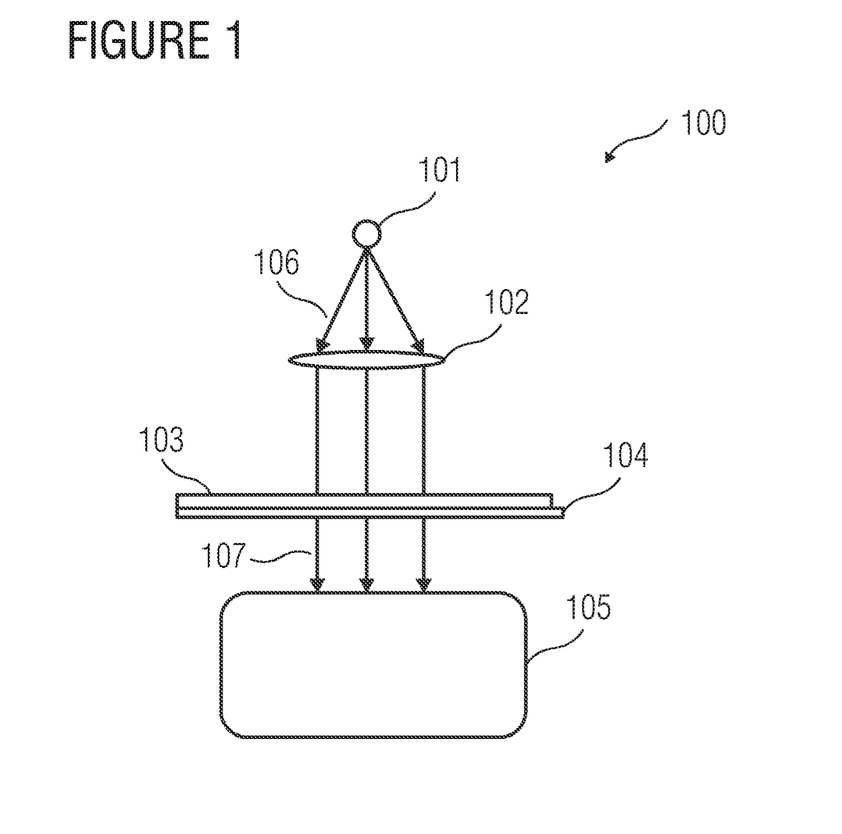
FIG. 1 illustrates an embodiment of a system for determining a concentration of one or more analytes in whole blood.

FIG. 1 illustrates an embodiment of a system 100 for determining a concentration of one or more analytes in whole blood. The system 100 comprises a light source. The light source 101 may be, for example a broadband light source capable of emitting light at varying wavelengths. In an embodiment, the emitted light may have a wavelength in the range between 400 nm and 650 nm. The system 101 further comprises a collimator 102 configured to collimate the light emitted from the light source 101 on to a channel 103. The channel 103 may be, for example, a microfluidic channel that is configured to carry whole blood. The channel 103 may be composed of a transparent material such as, but not limited to, glass such that the light from the light source may pass through the surface of the channel, and interact with the whole blood. In an embodiment, the channel 103 may be embedded in a microfluidic chip. The depth of the microfluidic channel 103 may be in the range between 100 and 150 μm. The length and width of the channel may be in the range of 15 mm to 20 mm. Therefore, the amount of whole blood sample may between 10 and 50 μm.

In an embodiment, the channel 103 is in contact with an actuation module 104. The actuation module 104 may generate a cell-free plasma layer in the channel 103 from the whole blood, wherein the cell-free plasma layer is devoid of red blood cells. The actuation module, for example, may be configured to generate a dielectrophoretic environment in the channel 103. Dielectrophoresis is a phenomenon of applying a force on a dielectric particle when subjected to an electric field. Dielectrophoresis may cause dielectric polarization of particles thereby displacing positive charges in the direction of the field and the negative charges in the opposite direction. Therefore, in a whole blood sample, blood cells are separated from plasma as the cells move towards the direction of the electric field and a cell-free plasma layer is generated in the center of the channel 103. The actuation module 104 may be, for example, a pair of electrodes 104. The electrodes 104 are connected to an electric field so as to create a dielectrophoretic environment. In another embodiment, the electrodes 104 are connected to the channel 103 on the outer surface. The electrodes 104 may be spaced in the range of 2 to 10 mm. Application of a high frequency voltage to the electrodes 104 enables generation of a force gradient in the channel 103. This force gradient pushes the blood cells towards the boundary of the channel 103. The system 100 also includes an optical module 105 configured to determine the concentration of one or more analytes in the sample. The optical module 105 may be, for example, a spectrophotometer. The optical module 105 is configured to perform a quantitative measurement of analytes that may be present in a given sample as a function of wavelength. In an embodiment, the optical module 105 may be configured to measure blood gas concentrations in whole blood when the actuation module 104 is disconnected from the electric field and to measure free hemoglobin content when the actuation module 104 is connected to the electric field. The blood gas concentrations in whole blood are measured by analyzing analytes such as oxygen hemoglobin (O2Hb), non-oxygen carrying but normal hemoglobin (HHb), carboxyhemoglobin (COHb) and methemoglobin (MetHb).

Figure 2:
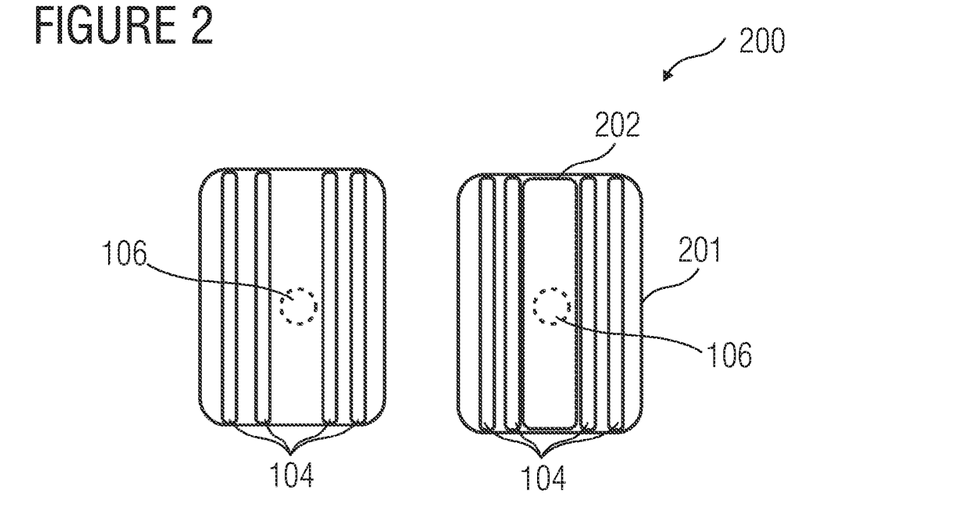
FIG. 2 illustrates an embodiment of a matrix for generation of cell-free plasma layer.

FIG. 2 illustrates an embodiment of a matrix 201 for determining the concentration of one or more analytes in whole blood. The matrix may be, for example a microfluidic chip. The matrix 201 includes a transparent medium. The transparent medium may be composed of, for example, glass. In an embodiment, the matrix 201 may include two microscopic slides placed on top of each other. The transparent medium has a channel 103. The channel 103 is configured to carry the whole blood sample. In an embodiment, the channel 103 has a depth in the range of 100 μm to 150 μm. The channel may have a length and width in the range of 15 to 20 mm. The matrix 201 further includes an actuation module 104 coupled to the matrix. The system 100 is also capable of determining hemolysis in the whole blood sample. In order to do so, system 100 creates a cell-free plasma layer 202. In particular, the actuation module 104 is used for generation of the cell free plasma layer 202. In an embodiment, the actuation module 104 includes one or more electrodes.

The configuration 200 illustrates the channel 103 comprising the whole blood sample and the electrodes 104 connected to the channel 103 on the outer surface of the matrix 201. The electrodes 104 are elongated and are in proximity to the channel 103. The length of the electrodes 104 extends in the direction of the flow of the whole blood sample in the channel 103. The electrodes 104 are coupled along the length of the matrix 201 at opposite ends such that the distance between the electrodes is in the range of 2 to 10 mm. Therefore, when a high voltage is applied to the electrodes 104, an electric field is generated in the center of the channel 103 in the matrix 201. In an embodiment, the electrodes 104 are microfluidic electrodes. The electric field may be switched on or off. In the absence of the electric field, the whole blood remains unseparated. When the high frequency voltage is applied to the electrodes 104, the blood cells are polarized, thereby causing the blood cells to move towards the electrodes 104. The cell-free plasma layer 202 is therefore generated in the center of the channel 103.

Hemolysis is a phenomenon of rupture of red blood cells causing a release of contents of the red blood cells such as hemoglobin into the plasma. The concentration of free hemoglobin in the plasma layer provides an indication of the extent of hemolysis in the whole blood sample. Accurate measurement of free hemoglobin may be obstructed by the presence of blood cells in the whole blood sample. Therefore, generation of the cell-free plasma layer 202 enables accurate and efficient measurement of free hemoglobin in the sample. The cell-free plasma layer is devoid of the blood cells. Therefore, in the absence of any obstructions, the cell-free plasma layer may be used for further analysis of analytes such as free hemoglobin. In alternate embodiments, the actuation module 104 may be configured to generate the cell-free plasma layer 202 in the microfluidic channel 103, for example, using acoustophoresis or thermophoresis.

Figure 3:
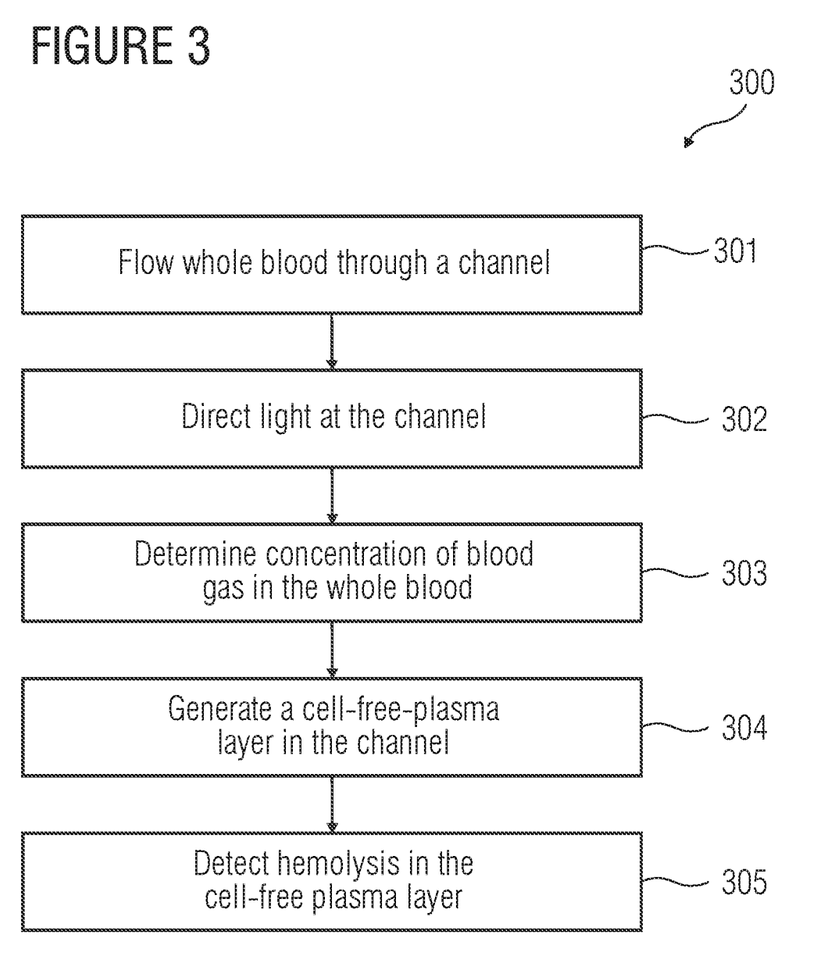
FIG. 3 illustrates a flowchart of an embodiment of a method of determining a concentration of one or more analytes in whole blood.

FIG. 3 illustrates a flowchart of an embodiment of a method 300 of determining a concentration of one or more analytes is the whole blood. The one or more analytes may include, for example, analytes required for the determination of blood gas concentrations; and free hemoglobin. At step 301 of the method 300, the whole blood sample is flowed through the channel 103. In an embodiment, the thickness of the sample in the channel is in the range between 100 and 150 μm. At step 302, light 106 from the light source 101 is directed at the channel 103 such that the light interacts with the whole blood sample. As the thickness of the sample is in the range between 100 and 150 μm, path length of the light in the channel is low. In the embodiment, the channel 103 is transparent, thereby enabling the light 107 to pass through the channel 103. At step 303, the concentration of blood gas in the whole blood is determined from the light 107 transmitted from the channel 103. The method steps of determining the concentration of blood gas in the whole blood is described in detail in FIG. 5. Determination of concentration of free hemoglobin may require generation of a cell-free plasma layer in the channel 103. Therefore, at step 304 of the method, a cell-free plasma layer is generated in the channel 103. Such cell-free plasma layer may be generated by the actuation module 104. The generation of the cell-free plasma layer in the channel 103 is described in detail in FIG. 2. At step 305 of the method 300, free hemoglobin, or hemolysis is detected in the plasma layer generated by the actuation module 104. The method steps of determining the concentration of free hemoglobin in the plasma layer is described in detail in FIG. 4.

Figure 5:
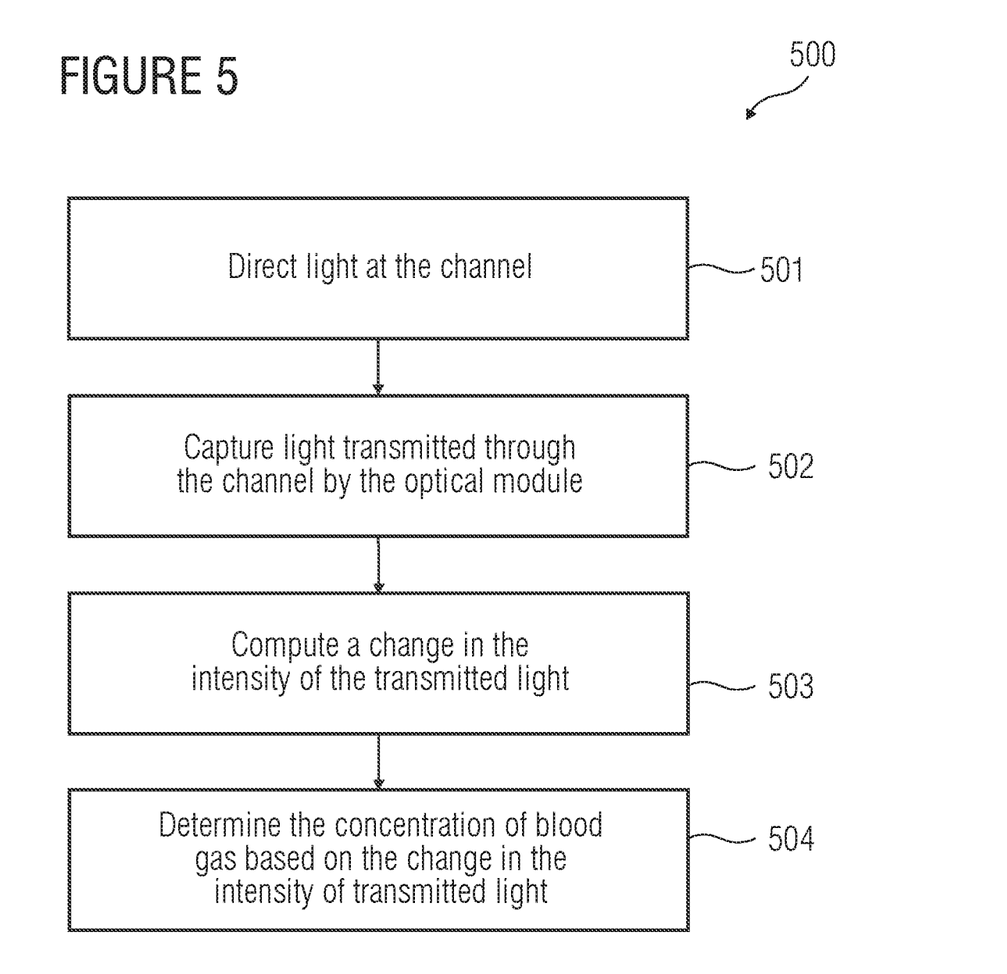
FIG. 5 illustrates a flowchart of an embodiment of a method of determining blood gas concentration in the whole blood sample.

FIG. 5 illustrates a flowchart of a method 500 of determining the blood gas concentration in the whole blood sample. At step 501, the channel 103 carrying the whole blood is illuminated with light 106 from the light source 101. In an embodiment, the whole blood sample may be illuminated with light 106 at varying wavelengths. Each wavelength may correspond to a specific analyte to be measured. The light 106 is collimated onto the channel 103 using a collimator 102. The light interacts with the whole blood in the channel 103 and may be absorbed due to the presence of blood cells. Such absorption may be based on the concentration of the corresponding analyte in the whole blood. Therefore, the absorption of light by the sample may produce a decrease in the intensity of the light 106 with which the channel 103 was illuminated. The transmitted light 107 is captured by the optical module 105 at step 502 and a change in the intensity of the transmitted light 107 in comparison with the illuminated light 106 is computed at step 503. The change in the intensity of the transmitted light 107 corresponds to absorbance of the whole blood. Therefore, based on the absorbance the concentration of the corresponding analyte in the whole blood is determined at step 504.

Figure 4:
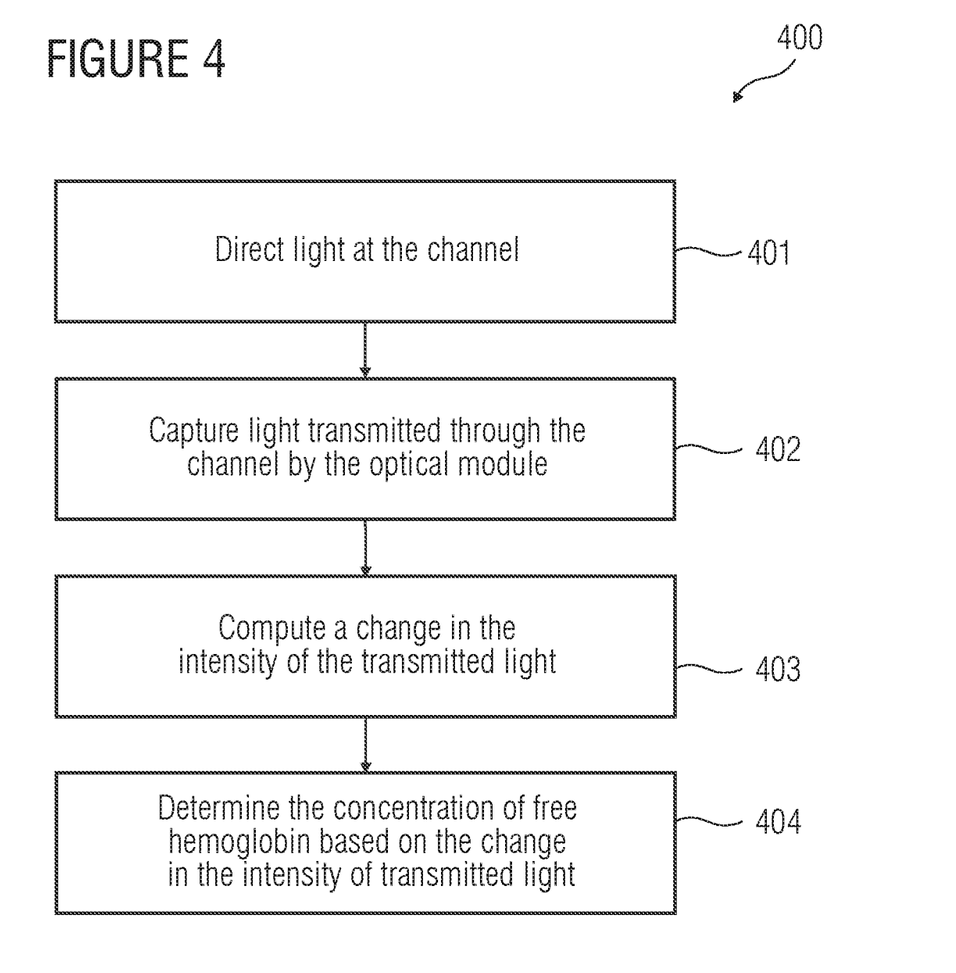
FIG. 4 illustrates a flowchart of an embodiment of a method of detecting hemolysis in the plasma layer.

FIG. 4 illustrates a flowchart of an embodiment of a method 400 of detecting hemolysis in the plasma layer 202. As described earlier, the actuation module 104 is configured to generate a layer of cell-free plasma in the channel 103 when connected to an electric field. The cell-free plasma layer 202 may be used for detection of hemolysis, i.e. presence of free hemoglobin. At step 401 of the method 400, light is directed at the channel 103 from the light source 101. In an embodiment, in order to determine the concentration of free hemoglobin in the plasma layer 202, determining the concentration of interfering analytes such as bilirubin and lipids may also be essential. The presence of bilirubin and lipids may also be detected in the same wavelength range as that of hemoglobin. Therefore, in order to accurately determine the presence of free hemoglobin in the plasma, the effect of the presence of bilirubin and lipids in the sample may have to be eliminated. Therefore, in an embodiment, the light 106 directed at the channel may be of varying wavelengths. Each wavelength may be specific to the analyte to be determined, i.e. the concentration of bilirubin, hemoglobin and lipids in the sample may be determined using different wavelengths respectively. In an embodiment, the light source may emit light having wavelengths in the range between 400 nm and 650 nm.

At step 402, the light transmitted 107 from the channel is captured by the optical module 105 and at step 403 a change in the intensity of the transmitted light 107, in comparison with the intensity of the illuminated light 106, is computed by the optical module 105. The change in the intensity of the transmitted light 107 may be due to absorption of light by the analytes in the plasma layer 202. The change in intensity corresponds to concentration of the analyte in the plasma. Therefore, at step 404, the concentration of the analyte in the plasma is determined based on the change in the intensity of the transmitted light 107. The determined concentrations of bilirubin and lipids may be used to eliminate the interference effect on the concentration of free hemoglobin in the cell free plasma layer 202.

The invention provides a single platform for accurate and efficient determination of blood gas and generation of cell-free plasma layer for hemolysis detection in a given whole blood sample. Therefore, requirement of more than one system for analysis of the blood sample is eliminated. This further enables analysis of blood samples to be faster and cost effective. The whole blood may also be retrieved from the channel for further analysis or downstream processing once the process of determination of the concentration of the analytes is completed.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

What is claimed is:

1. A system for determining a concentration of one or more analytes in whole blood, the system comprising:
a transparent channel configured to carry whole blood;
a light source configured to emit light on the transparent channel;
an actuation module associable with the transparent channel, wherein the actuation module comprises a pair of electrodes associated with opposite ends of the transparent channel, wherein the pair of electrodes are configured to generate a dielectrophoretic environment in the transparent channel and thereby generate a cell-free plasma layer from the whole blood in the center of the transparent channel when the pair of electrodes are subjected to an electric field; and
an optical module associable with the transparent channel, wherein the optical module is configured to determine, within the transparent channel, blood gas concentrations in unseparated whole blood and free hemoglobin concentration in the cell-free plasma layer; and
wherein the optical module is configured to determine blood gas concentrations in the unseparated whole blood in the transparent channel by capturing light transmitted from the transparent channel and computing a change in the intensity of the transmitted light, wherein the change in the intensity correlates to the concentration of the blood gas in the whole blood,
wherein the optical module is configured to determine free hemoglobin concentration in the cell-free plasma layer in the transparent channel by capturing light transmitted from the transparent channel and computing a change in an intensity of the transmitted light, wherein the change in the intensity correlates to free hemoglobin in the whole blood.

2. The system according to claim 1, wherein the transparent channel configured to carry blood is a transparent microfluidic channel.

3. The system according to claim 1, wherein the pair of electrodes are microfluidic electrodes.

4. The system according to claim 1, wherein the pair of electrodes are associated with an outer surface of the transparent channel.

5. The system according to claim 4, wherein the pair of electrodes are coupled along a length of the outer surface of the transparent channel at opposite ends of the transparent channel such that the distance between the electrodes is in a range of from 2 to 10 mm.

6. The system according to claim 1, wherein the optical module is a spectrophotometer.

7. A method of determining a concentration of one or more analytes in whole blood, the method comprising:
- flowing the whole blood through a transparent channel;
- directing light at the transparent channel;
- determining the concentration of a blood gas in the whole blood in the transparent channel by capturing light transmitted from the transparent channel and computing a change in the intensity of the transmitted light, wherein the change in the intensity correlates to the concentration of blood gas in whole blood;
- generating a plasma layer from the whole blood in the transparent channel by subjecting the whole blood to dielectrophoretic environment which causes the blood cells to separate from plasma as the blood cells move towards the direction of the electric field and generate a cell-free plasma layer in the center of the transparent channel; and
- detecting hemolysis in the plasma layer in the transparent channel by directing light at the plasma layer, capturing light transmitted from the transparent channel, and computing a change in an intensity of the transmitted light, wherein the change in the intensity correlates to a concentration of the analyte in the plasma layer, wherein the analyte is released in the plasma layer due to hemolysis.

* * * * *